United States Patent
Krajíček

(12) 
(10) Patent No.: US 6,203,490 B1
(45) Date of Patent: Mar. 20, 2001

(54) MYOCARDIAL STABILIZER

(76) Inventor: Milan Krajíček, Chalupkova 1368, 149 00 Praha 4 (CZ)

( * ) Notice: Subject to any disclaimer, the term of this patent is extended or adjusted under 35 U.S.C. 154(b) by 0 days.

(21) Appl. No.: 09/322,947

(22) Filed: May 28, 1999

(30) Foreign Application Priority Data

May 28, 1998 (CZ) ..................................... 1640-98

(51) Int. Cl.[7] .............. A61F 2/00; A61F 13/00
(52) U.S. Cl. ............................................. 600/37
(58) Field of Search ................ 600/37, 201; 128/897, 128/898, 899

(56) References Cited

U.S. PATENT DOCUMENTS 6,063,021 * 5/2000 Hossain et al. ..................... 600/37

* cited by examiner

Primary Examiner—Samuel G. Gilbert
(74) Attorney, Agent, or Firm—Akin, Gump, Strauss, Hauer & Feld, L.L.P.

(57) ABSTRACT

For some types of cardiac operations it is advantageous to execute the procedure on the working, beating heart, i.e., without arresting the heart and imposing extra-corporeal circulation on the heart. However, where such a procedure is performed, it is simultaneously necessary to immobilize the appropriate myocardial part during the time required for the surgical procedure. For this purpose, a device is provided having a solid part which has a source of a magnetic field to be applied externally to the area of the cardiac muscle to be immobilized, and ferromagnetic fibers which are introduced into the myocardium of this part of the heart muscle in the desired length, position and form. During the existence of the induced magnetic field, the ferromagnetic fibers are attracted toward the solid part of the device. By compression of the myocardium between the ferromagnetic fibers and the part inducing the magnetic field, and immobilization of this myocardial region is achieved.

19 Claims, 4 Drawing Sheets

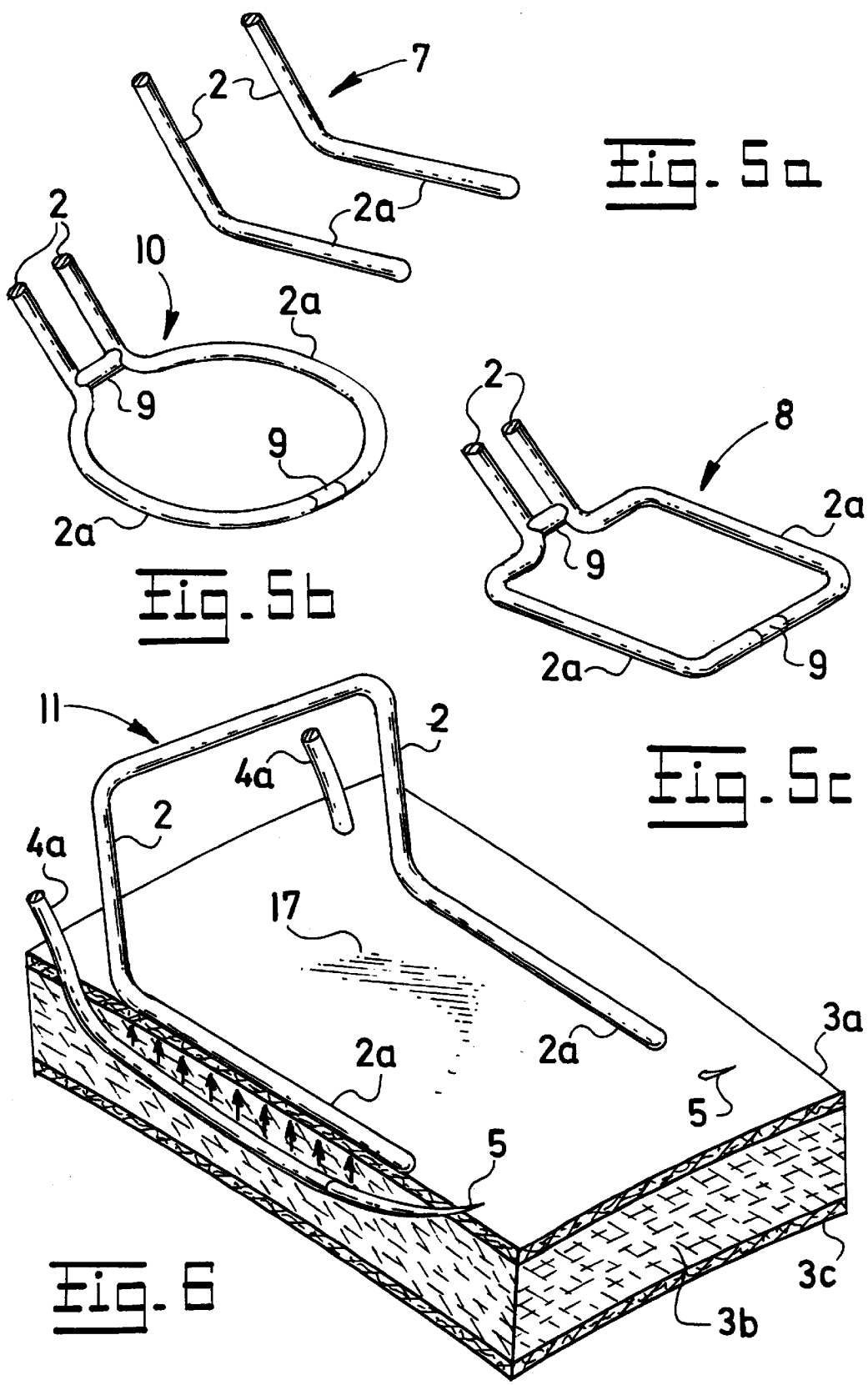

MYOCARDIAL STABILIZER

BACKGROUND OF THE INVENTION

The present invention relates to a myocardial stabilizer for immobilizing a particular part of a working heart, so as to enable an indicated operation on heart wall structures, particularly the coronary arteries.

For illustration of the invention there may be considered the most frequent cardiosurgical operation, which is indisputably a direct revascularization of the myocardium through operation on coronary arteries. Most of these operations are still performed using extra-corporeal circulation on an arrested heart. In recent years, however, a method has been used more and more often in indicated cases where reconstruction, i.e., peripheral anastomosis of vascular substitute, is feasible on a working heart without its arrest and without using extra-corporeal circulation. This means, of course, the risk in these operations is taken to another, substantially lower level in order.

Anastomosis of the vascular substitute, most often of the patient's veins themselves, is a delicate operation. When applied to as delicate an artery as the coronary artery, a necessary and sufficient condition is a perfect technical execution for the operation to be viewed as successful. The coronary artery is located under the epicardium, and its movement is therefore connected with the heart muscle movement itself. Since the frequency of cardiac beats cannot be decreased below a certain level, this method has its physiological limits. Thus, there is a certain contradiction in the necessity of a perfect placing of stitches into edges of a longitudinally opened coronary artery, on the one hand, and a continuous movement of the operation field, i.e., the heart and artery, on the other hand.

At the present time, there are two devices which are applied to immobilize the portion of the coronary artery to be operated on during the operation. In principle, these involve something like a fork with arms either joined together or individually controlled. One method brings calm to the operation field by applying pressure on a specific point of the cardiac muscle. Another method consists in contacting a respective area of the cardiac muscle with a surface of the device which is provided with suction holes, so that the muscle area is sucked into the device at the contact point of the device and the cardiac muscle.

These devices are much in use at the present time. However, they have their disadvantages. Thus, the handling of a device using pressure cannot exclude the possibility of pressure damage to the cardiac wall structures, particularly with longer operations and the application of higher pressures. Other disadvantages of these methods include limits on pressure adjustment, the tendency of a moving cardiac muscle to slip out from under the device, and the impossibility of using these devices, in practice, for all coronary arteries now being reconstructed, regardless of their anatomical position.

The device using a vacuum or suction principle is an improvement over the previous one. The stabilizer OCTOPUS™ is considered the most acceptable. It is characterized by two independent flexible arms with terminals of various forms provided with various numbers of suction holes. The bases of the arms and the whole suction mechanism are placed outside the operating table, and the surgeon handles only the terminals, which he can place as desired and then clamp the terminal walls on a given area by connecting the suction. This enables access even to coronary arteries on the adverse side of the heart.

A disadvantage of this procedure is again the possible damage of the cardiac muscle structures by negative pressure and generation of slight subepicardial and myocardial bleeding, the long-term consequences of which are not yet quite clear. In principle, there arises a range of small phenomena which are colloquially referred to in some places as "suckflecks."

Both of these devices are, in their various modifications, also relatively quite expensive. Therefore, there is a need in the art for a myocardial stabilizer to immobilize a particular part of a working heart to enable an operation on the coronary arteries, without the disadvantages of the above-described prior art devices and procedures.

BRIEF SUMMARY OF THE INVENTION

The above-described deficiencies of the prior art are overcome or alleviated by the device of the present invention for local stabilization of the cardiac muscle, which includes two physically independent but functionally dependent parts. One part comprises a permanent magnet or adjustable electromagnetic core, roughly resembling a fork, having a bent arm or terminal end which forms a contact surface for application to an external surface of the heart, with the contact surface having sufficient size or length to immobilize the desired area of the heart. The second part comprises a fiber made of ferromagnetic, magnetically hard material which is drawn through the myocardium at a desired point and in the desired length of the area to be immobilized.

After drawing or inserting the ferromagnetic fiber into the desired area of the cardiac muscle, the contact surface of the magnet is placed over the area of the myocardium containing the ferromagnetic fiber, so that the magnetic force attracts or draws the fiber toward the contact surface of the permanent magnet or electromagnet. As a result, the contact surface of the magnet and the ferromagnetic fiber hold the portion of the myocardium between them and thereby immobilize this area of the cardiac muscle. By providing two ferromagnetic fibers at opposite edges of the myocardium to be immobilized, with the two fibers being spaced at approximately the same distance as two magnet contact surfaces, so that each ferromagnetic fiber has its independent magnet to which the fiber is attracted, a good immobilization of the area of the heart muscle bounded by these fibers can be achieved.

The device according to the invention uses a magnetic induction effect in a stationary magnetic field. Both the principle of the invention and its practical use are relatively simple. A model stationary magnetic field is realized approximately by the field between discordant extensive (oppositely charged) poles of a magnet. The magnetic field is characterized by a vectorial variable called magnetic induction. The unit of magnetic induction is TESLA (T); and the magnitude of the magnetic induction of the field, e.g., with current permanent magnets, is $10^{-1}$ to $10^{-2}$ T. Of course, in principle, there are magnets, particularly electromagnets, which can be made whose field size values reach a magnitude on the order of units of TESLA. For reference purposes, it is noted that the earth within our geographic latitudes has a magnetic induction on the order of $10^{-5}$ T.

It is not critical for the device according to the present invention how the magnetic field is generated, whether by permanent magnet or by electromagnetic induction, either with a classic electromagnet or solenoid. The theory and practice of using a magnetic field are widely known per se in many fields, and the principle of its effect is always the same.

The size of the magnetic induction depends to a considerable extent on the s.c. environmental permeability within the magnetic field. This can be demonstrated by the example of an electromagnetic coil. Thus, steel has a very high relative permeability, and therefore the magnetic field induction of a coil wound on a closed steel core is much higher than for the same coil without a core. Three types of materials may be considered according to the values of their relative permeability, depending on the arrangement of the magnetic fields of the individual atoms. The highest values are those of s.c. ferromagnetic materials, whose atomic arrangement considerably magnifies the magnetic field. For example, the relative permeability of steel is $\mu r=8,000$.

Even a weak external magnetic field on a ferromagnetic material is sufficient to generate such an arrangement of atoms that the magnetic field becomes magnified. The material becomes magnetized, and the magnet field remains therein even after removing the external effect. Although the number of ferromagnetic materials is not high (iron, cobalt, nickel, and their alloys, as well as some others not containing these elements), they have considerable practical importance. It must be understood, however, that ferromagnetism of these materials is shown only in their crystalline state. It is therefore a property of the material structure, and not of the individual atoms. Among the ferrimagnetic materials are also those which are classified as ferrimagnetic, i.e., ferrites. These are generally iron oxide compounds or oxides of other metals, such as molybdenum. Their relative permeability is on the order of $\mu r=10^2$ to $10^3$. They are largely applied particularly as permanent magnets.

Based upon the above, the principle of use of the present invention can be understood. Thus, in general, at the point of required immobilization of the cardiac muscle, preferably not less than two fibers made of ferromagnetic material are drawn through the muscle, particularly the myocardium, to an effective length corresponding to a dimension of the area to be stabilized. A contact element capable of inducing a magnetic field, based either on the principle of a permanent magnet or an electromagnet, is applied to an external side of the muscle at the same point of desired immobilization. This contact element may be in the form of individual arms or arms which are magnetically connected, or may take a variety of other shapes. If the magnetic field applied by the contact element is sufficiently strong (intense), the fibers of ferromagnetic material will be attracted or drawn toward the magnet arms of the contact element, thereby immobilizing the portion of the cardiac muscle within the span of the contact element and the fibers. The arms of the magnet may have a rigid or flexible form, but should not be so flexible as to be unable to firmly hold the portion of the muscle to be immobilized. They may either stretch from a base outside of the operating field or be fixed by action of the magnetic field directly to a frame made of ferromagnetic material in the operating field.

The cardiac muscle does not become damaged by drawing the fibers through the muscle, since in any event stimulation electrodes are drawn through the muscle prior to termination of the operation. Also, an appropriate control of the magnetic field intensity may affect the power needed for the fibers to be drawn to the magnet, thus minimizing any accidental danger of pressure damage.

As used herein, the term "fiber" is used not only in its generally understood sense of a thread or filament, but is also intended to include more rigid and substantial structures such as pins, needles, safety pins or fixation tacks, all made of a ferromagnetic material.

BRIEF DESCRIPTION OF THE SEVERAL VIEW OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings which illustrate the invention schematically:

FIGS. 5a, 5b and 5c are perspective views of other possible forms for the magnet arms of a contact element of the invention for immobilizing an area of the cardiac muscle;

FIG. 6 is a perspective view of an embodiment of the invention using a permanent magnet, shown in operation in a manner similar to FIG. 3.

DETAILED DESCRIPTION OF THE INVENTION

Figure 1:
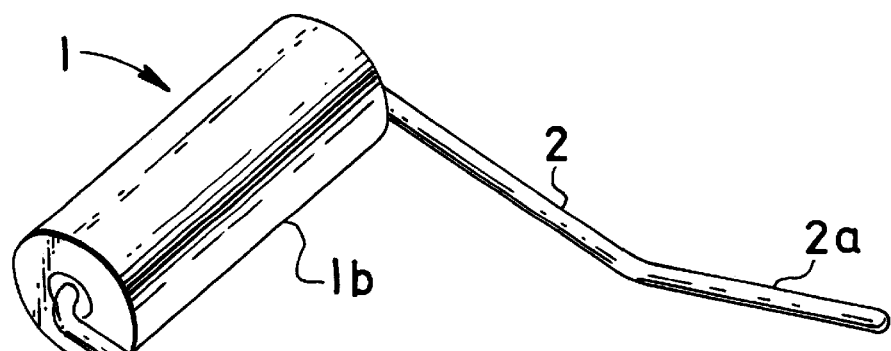
FIG. 1 is a perspective view of one embodiment of a device according to the invention, showing two magnet arms extending from an electromagnetic core.
Figure 2A:
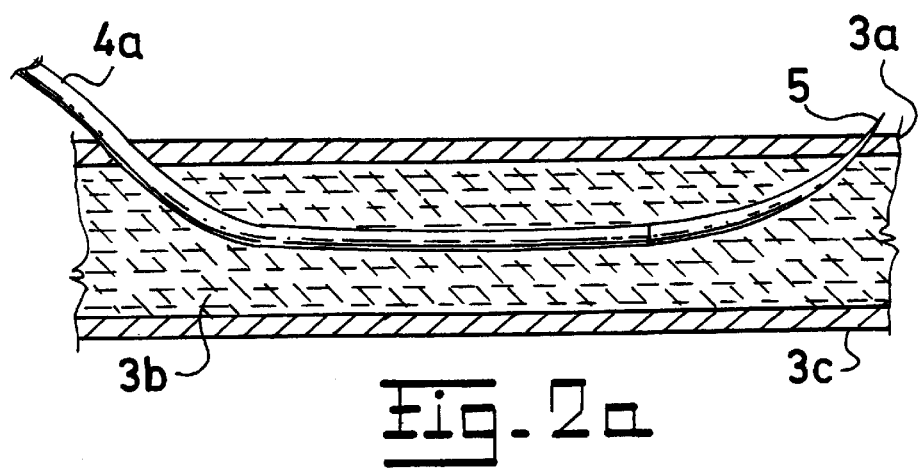
FIGS. 2a and 2b are simplified cross-sectional side views through the muscle of the cardiac wall, illustrating two different types of ferromagnetic fibers according to the invention and different possible locations for drawing them through the muscle.
Figure 2B:
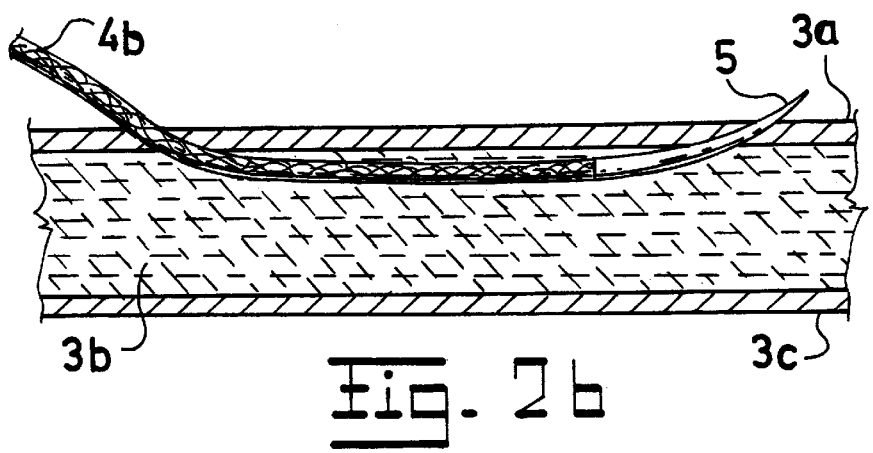
Figure 3:
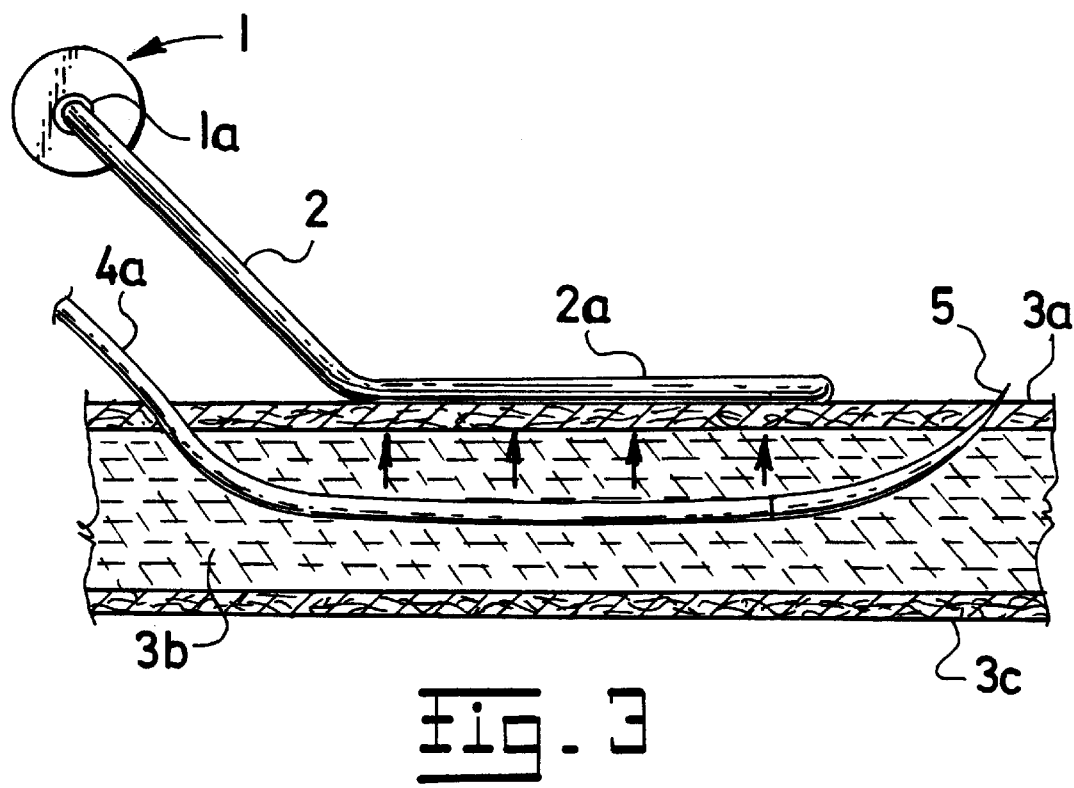
FIG. 3 is a side view, partially in section, showing the contact element of FIG. 1 and the ferromagnetic fiber of FIG. 2a in operation, with the vertical arrows indicating the direction in which the fibers are drawn toward the magnet.

Referring to FIGS. 1–3, an embodiment of the invention is shown in which the contact element for placing externally on the heart wall comprises an electromagnet, generally designated by 1, which consists of an electromagnetic core 1a and an electromagnetic coil 1b. Extending from the core 1a are two parallel magnet arms 2 which are bent at their ends to form contact surfaces 2a of the contact element portion of the device, as shown in FIG. 1. The magnet arms 2 may be made of any suitable material in which a magnetic field may be induced by the electromagnet 1. The arms may be the ends of a continuous wire or rod which extends through the core 1a or may be separate wires or rods attached to the core 1a. The contact surfaces 2a have a length corresponding to the area of the heart muscle to be stabilized or immobilized.

As shown in FIGS. 2a and 2b, fibers 4 of ferromagnetic material are inserted or drawn through the cardiac muscle 3, preferably by a needle 5 having a curved shape. The cardiac muscle 3 consists of three basic layers, namely the epicardium 3a which is the top or outer surface layer of the cardiac muscle, the myocardium 3b which is the central muscle layer itself, and the endocardium 3c which is the internal structure of the cardiac muscle. In FIG. 2a the fiber 4a is drawn through the myocardium 3b at approximately the center of its thickness, whereas in FIG. 2b the fiber 4b is drawn through the myocardium 3b at a location close to the epicardium 3a.

The fiber 4 may take various forms. In FIG. 2a fiber 4a is a monofilament of ferromagnetic material, whereas in FIG.

2b the fiber 4b is a multifilament fiber or thread made of ferromagnetic filaments spun or otherwise adhered together. In both of these instances, the fiber is preferably flexible so that it may be easily drawn through the myocardium in the same manner as a suture. However, it will be understood that a rigid or semirigid fiber, such as a pin, needle or tack made of ferromagnetic material could be used for insertion into the myocardium. For example, a double fiber in a form similar to safety pin could be used to provide the fibers of ferromagnetic material for use in the present invention.

Referring to FIG. 3, the contact element of FIG. 1 and the fiber 4a of FIG. 2a are shown in operation. At least two such fibers 4a are drawn through the myocardium 3b by needles 5. In the case of using two fibers 4a, these are inserted at a spacing corresponding approximately to the lateral spacing of the magnet arms 2, or more exactly the contact surfaces 2a of the magnet arms, as illustrated more clearly in FIG. 6. Thus, in operation, it is desired that the contact surfaces 2a lie approximately above (looking from the interior to the exterior of the heart wall) and parallel to the respective fibers 4a which have been inserted into the myocardium.

The contact surfaces 2a of the contact element of the device are spaced at a distance which corresponds to the width of the area of the cardiac muscle which is desired to be immobilized. To begin the operation, the two or more ferromagnetic fibers 4 are drawn through the myocardium 3b at the desired depth and at a spacing which encompasses the desired area to be immobilized. The contact surfaces 2a of the contact element are then placed on the exterior of the heart wall above and parallel to the previously inserted fibers, and the electromagnet 1 is then turned on. The electromagnet 1 is preferably capable of generating a magnetic induction of at least $10^{-2}$ T, and the magnetic induction may be adjusted depending upon the field strength needed to attract the ferromagnetic fibers, which depends in part on the depth at which the fibers have been inserted. When the electromagnetic 1 is turned on, the fibers 4a are drawn or attracted toward the contact surfaces 2a, as shown by the vertical arrows in FIG. 3, and the cardiac muscle area lying between the fibers 4a and the contact surfaces 2a is thereby immobilized.

Figure 4:
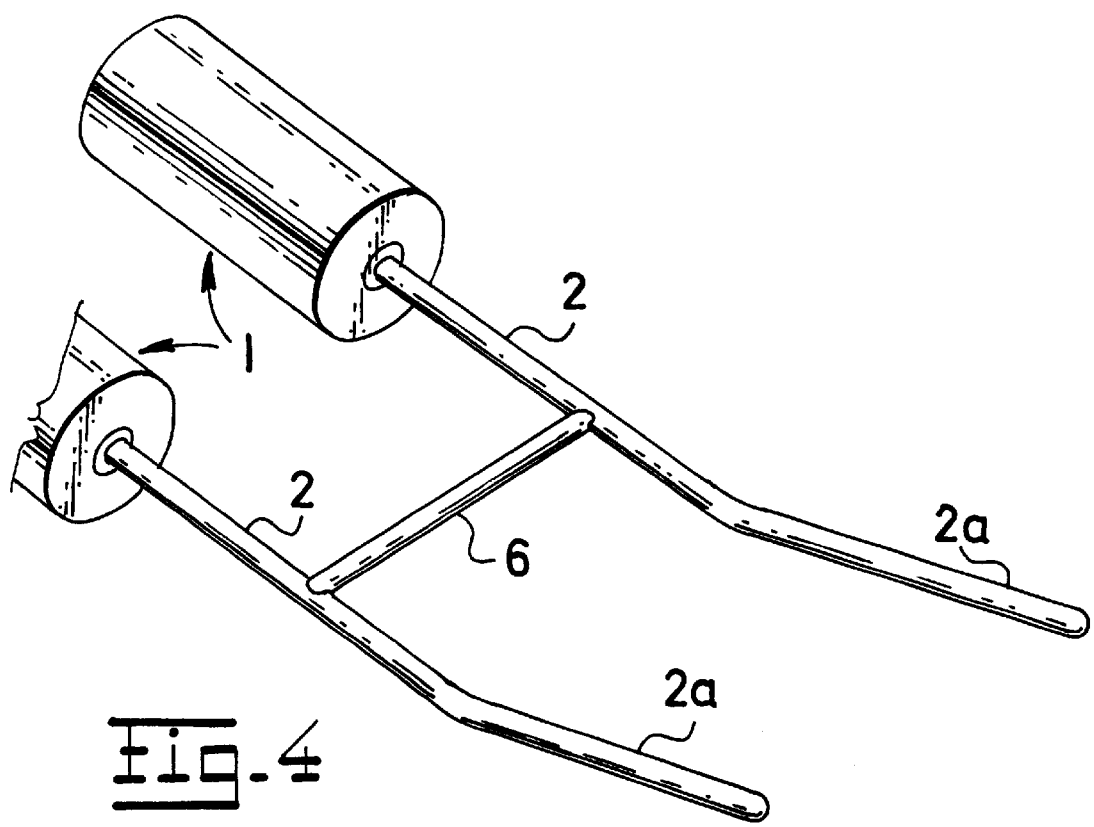
FIG. 4 is a perspective view of another embodiment of a contact element according to the invention, having arms with independent electromagnets, with the arms being connected by a non-magnetic link.

Referring to FIG. 4, another embodiment of the invention is illustrated in which the contact element portion of the device consists of two independent magnet arms 2 which are each equipped with its own independent electromagnet 1. As with the contact element of FIG. 1, the terminal ends of the magnet arms 2 are bent to form contact surfaces 2a having a length corresponding approximately to the size of the area to be immobilized. The independent electromagnets 1 are also capable of generating a magnetic induction of at least $10^{-2}$ T.

In the embodiment of FIG. 4, the independent magnet arms 2 are connected by a non-magnetic link 6 for ease of handling and accurate spacing of the contact surfaces 2a. However, it will be understood that the magnet arms 2 could be non-linked (see FIG. 5a) and freely maneuverable, and could even be brought into the operating field from opposite sides, while connected to an activating base outside of the operating table. In any event, the operation of these independent magnet arms 2 is essentially the same as described in connection with FIGS. 1–3, wherein the fibers 4 are first drawn through the myocardium, the contact surfaces 2a are placed above the fibers, and the electromagnet is turned on to cause the fibers to be attracted to the contact surfaces for immobilization of the area of the heart muscle delimited by the fibers and contact surfaces.

Referring to FIG. 5, there are shown several possible forms of the magnet arms 2 of the contact element portion of the device according to the invention, although it will be understood that other possible forms and shapes are conceivable. For ease of illustration, the electromagnet(s) 1 are not shown in these figures, but are attached to the arms in a manner similar to FIGS. 1 and 4. FIG. 5a illustrates the arms 2 with contact surfaces 2a of a contact element 7, wherein the magnet arms are independent and unlinked as just described.

FIGS. 5b and 5c illustrate magnet arms 2 of contact elements 10 and 8, respectively, in which the contact surfaces 2a are connected by non-magnetic connectors 9 to form a substantially circular contact element 10 (FIG. 5b) and a substantially square contact element 8 (FIG. 5c) for surrounding or delimiting the surface area of the cardiac muscle to be immobilized. As will be readily understood, contact elements having such shapes may require different types of insertion of the ferromagnetic fibers and/or the use of more than two ferromagnetic fibers. For example, when using the circular element 10 of FIG. 5b, two or more ferromagnetic fibers could be drawn through the myocardium in a semicircular or other curved path. Similarly, when using the substantially square element 8 of FIG. 5c, four ferromagnetic fibers could be inserted in the myocardium, with one parallel to each side of the square. The devices of FIG. 5 are used in essentially the same manner as those of FIGS. 1–4 with magnets capable of generating a magnetic induction of at least $10^{-2}$ T.

Referring to FIG. 6, an embodiment of the invention is shown similar to that of FIGS. 1–3, except that the magnet is a permanent magnet, indicated generally by 11, made of a continuous rod of permanent magnetic material bent into the shape of a double-armed fork with magnet arms 2 whose bent terminal ends form contact surfaces 2a. As with FIG. 3, the ferromagnetic fibers 4a are shown drawn through the myocardium 3b by needles 5 at a spacing corresponding to the magnet arms 2 of the fork of the permanent magnet 11, which is also capable of generating a magnetic induction of at least $10^{-2}$ T. However, in this case, instead of having to turn the magnet on, as soon as the permanent magnet 11 is placed on the external surface of the heart wall, the fibers 4a are immediately drawn toward the contact surfaces 2a of the magnet, and the area 17 encompassed by these contact surfaces and fibers is immobilized by the magnetic attraction (shown by the vertical arrows in FIG. 6).

As discussed above in connection with FIGS. 4 and 5a, the permanent magnet 11 could instead consist of two independent permanent magnets fixed on independent carriers, for example, independent flexible carriers attached to a base located outside of the operating table. These independent permanent magnets can be operated and applied in the same manner as discussed above, except that again the attraction of the ferromagnetic fibers and the consequent immobilization of the delimited area of the heart muscle occurs essentially immediately as the magnets are brought over the area of the inserted fibers and placed against the exterior heart wall.

Figure 7:
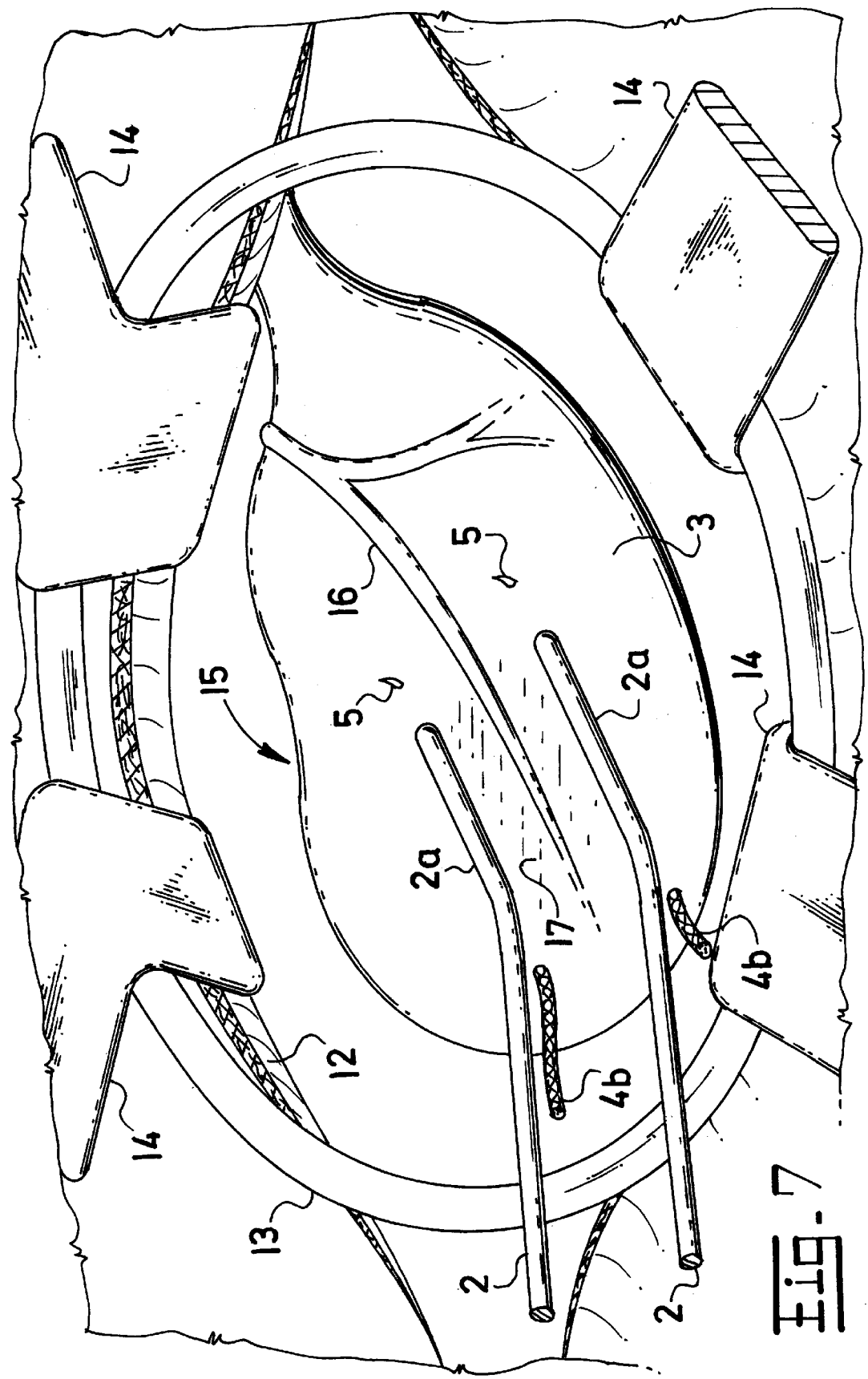
FIG. 7 is a simplified view of an operating field in the area of the heart, showing an embodiment in which the magnet arms are fixed to a frame of ferromagnetic material.

Referring finally to FIG. 7, an embodiment of the invention is shown in which a rigid circular frame 13 of ferromagnetic material is placed around the operating field 12, which in this case is the open sternum above the heart, indicated generally by 15. To this rigid circular frame 13 are fixed by magnetic induction dilating spoons or hooks 14, also made of ferromagnetic material, which support the circular frame around the operating field. Also fixed to the circular frame 13 are the central or upper parts of the magnet arms 2 of either an electromagnetic or permanent magnet according to the present invention. These magnet arms 2 are also fixed in place on the circular frame 13 by magnetic induction.

For operation on a coronary artery 16 without the necessity of using extra-corporeal circulation on an arrested heart, an area 17 of the cardiac muscle 3 is immobilized by first inserting ferromagnetic fibers 4b through the myocardium by means of needles 5 along two side edges of the area 17 to be immobilized. Contact surfaces 2a of magnet arms 2 are then placed against the external heart wall along the same side edges of the area 17 above the ferromagnetic fibers 4b, and the area 17 of the cardiac muscle is immobilized by application of the permanent magnetic or electromagnetic field, which draws the ferromagnetic fibers upward toward the contact surfaces 2a of the magnet arms 2. In this manner, the myocardium surrounding the coronary artery 16 is stabilized to allow the performance of a cardiosurgical operation without arresting the heart, and thereby reducing the risk of such an operation.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

I claim:

1. A device for local stabilization or immobilization of an area of cardiac muscle of a working heart, comprising at least one ferromagnetic fiber (4) for insertion into the cardiac muscle along a periphery of the area of the muscle (3) to be stabilized, at least one elongated magnet arm (2) having a contact surface (2a) for contacting an external surface of the muscle adjacent said fiber, and a source of magnetic induction (1, 11) connected to said magnet arm (2) for applying a magnetic field to cause attraction between the fiber and the contact surface sufficient to stabilize the muscle.

2. The device according to claim 1, wherein the source of magnetic induction is an electromagnet.

3. The device according to claim 1, wherein the at least one magnet arm and the source of magnetic induction together comprise a rod of permanent magnetic material.

4. The device according to claim 1, wherein the source of magnetic induction has an induction rating of at least $10^{-2}$ TESLA.

5. The device according to claim 1, wherein the at least one ferromagnetic fiber is a monofilament fiber.

6. The device according to claim 1, wherein the at least one ferromagnetic fiber is a multifilament fiber.

7. The device according to claim 1, wherein a needle (5) is attached to the fiber for drawing the ferromagnetic fiber through the cardiac muscle.

8. The device according to claim 1, wherein the fiber has an effective length corresponding to at least one dimension of the area of the muscle to be stabilized.

9. The device according to claim 8, wherein the contact surface has a length corresponding approximately to the effective length of the fiber.

10. The device according to claim 1, wherein the contact surface comprises a terminal end of the at least one elongated magnet arm and is bent away from the longitudinal axis of the magnet arm.

11. The device according to claim 1, comprising two elongated magnet arms extending parallel to one another from the source of magnetic induction and spaced from each other at a distance corresponding approximately to a dimension of the muscle area to be stabilized.

12. The device according to claim 11, wherein each arm is connected to its own independent source of magnetic induction.

13. The device according to claim 11, wherein the two magnet arms are connected by a non-magnetic link (6).

14. The device according to claim 13, wherein each magnet arm has the form of a semicircle with their respective openings facing each other to form a circle with non-magnetic links at junctions between the semicircles.

15. The device according to 13, wherein each of the magnet arms is bent rectilinearly with openings facing each other to form a square with non-magnetic links connecting the magnet arms at their junctures.

16. The device according to claim 1, wherein the at least one magnetic arm is flexible and has a base located outside an area of an operating table where an operation on an area of the cardiac muscle of a working heart is taking place.

17. The device according to claim 1, further comprising a rigid circular frame (13) of ferromagnetic material for placing around an operation field, and a plurality of removable dilation spoons or hooks (14) of ferromagnetic material, which can be fixed on the circular frame by magnetic induction.

18. A method for local stabilization or immobilization of an area of cardiac muscle of a working heart, comprising inserting at least one ferromagnetic fiber (4) into the cardiac muscle along a periphery of the area of the muscle (3) to be stabilized, applying a solid contact surface (2a) to an external surface of the muscle adjacent to the inserted fiber, and applying a source of magnetic induction to said contact surface to cause attraction between the fiber and the contact surface sufficient to stabilize the muscle.

19. The method according claim 18, wherein at least two ferromagnetic fibers are inserted in the muscle along opposite peripheral edges of the area of the muscle to be stabilized, and two contact surfaces are applied on the external surface of the muscle adjacent to said inserted fibers.

* * * * *